United States Patent
Shen et al.

(10) Patent No.: US 8,812,090 B2
(45) Date of Patent: Aug. 19, 2014

(54) CALIBRATION METHOD OF ELECTROCARDIOGRAM SIGNALS AND THE APPLICATION PROGRAM FOR THE SAME

(75) Inventors: Tsu-Wang Shen, Hualien (TW); Shan-Chun Chang, Hualien (TW)

(73) Assignee: Tzu Chi University, Hualien County (TW)

( * ) Notice: Subject to any disclaimer, the term of this patent is extended or adjusted under 35 U.S.C. 154(b) by 258 days.

(21) Appl. No.: 13/455,332

(22) Filed: Apr. 25, 2012

(65) Prior Publication Data

US 2013/0190635 A1 Jul. 25, 2013

(30) Foreign Application Priority Data

Jan. 20, 2012 (TW) .............................. 101102648 A

(51) Int. Cl.
*A61B 5/0402* (2006.01)
(52) U.S. Cl.
USPC ........................................................ 600/509
(58) Field of Classification Search
CPC ..... A61B 5/04; A61B 5/04012; A61B 5/0402
USPC ........................................................ 600/509
See application file for complete search history.

(56) References Cited

U.S. PATENT DOCUMENTS 5,381,351 A * 1/1995 Kwong et al. .................. 702/88
8,351,887 B2 * 1/2013 Stevenson ................... 455/234.1

* cited by examiner

*Primary Examiner* — Amanda Patton
(74) *Attorney, Agent, or Firm* — Chun-Ming Shih; HDLS IPR Services

(57) ABSTRACT

A calibration method of electrocardiogram signals and the application program for the same. The method comprises steps of receiving an uncalibrated/unidentified electrocardiogram signal of a user, calculating the ratio of the distance length of an uncalibrated/unidentified electrocardiogram signal and the distance length of an electrocardiogram template, then generating a trigonometric value which corresponds with a trigonometric projection degree according to the ratio. Next step is to set a characteristic point of the uncalibrated electrocardiogram signal as an axis anchor point of the trigonometric projection for attaining a displacement. Lastly, perform the calibration on the unidentified electrocardiogram signal according to the generated trigonometric value which corresponds with trigonometric projection degree and the attained displacement. Then perform identification comparison of the unidentified electrocardiogram signal and the saved electrocardiogram template for further authorization.

12 Claims, 10 Drawing Sheets

CALIBRATION METHOD OF ELECTROCARDIOGRAM SIGNALS AND THE APPLICATION PROGRAM FOR THE SAME

BACKGROUND OF THE INVENTION

1. Field of the Invention

The present invention relates to electrocardiogram (ECG) identification and/or verification technologies, in particulate relates to a method for calibrating and normalizing ECG signals used in ECG identification systems for enhancing the identification rate under various heart rates.

2. Description of Prior Art

In recent years, the biometrics technologies are applied in many commercial products, for example, the fingerprint identification and the iris identification are widely utilized in daily life. Biometrics technologies are essential for user identification and gradually improve other traditional security means such as ID cards, passwords, and keys because they have delivered the security mechanisms which are more convenient and secure.

Though, the mentioned fingerprint and iris identification methods are applied in current commercial products. However, the researches indicate some concerning facts on unauthorized duplicates or counterfeits with current biometric systems. For example, users may leave their fingerprints on a touched surface. Therefore, a third party may create a fingerprint duplicate based on that surface imprint. Further, if a third party gives an iris identification sample wearing specialized lens and duplicates the lens to other people, anyone wearing the lens pass the comparison because of the specialized lens.

Recent researches also shows, in addition to the known arts such as fingerprints and iris bio characteristics, the human ECGs are different from person to person and qualify to utilize in identification. FIG. 1 is a schematic diagram of the ECG signal monitoring system according to the prior art. A user 1 measures the ECG of oneself by an ECG monitoring device 2, and the ECG monitoring device 2 records a series of ECG 3. A normal ECG 3 from each individual typically has characteristic points P, Q, R, S, T, yet the relative positions vary, whereby the comparison of the characteristic points are used for determining authorization of the user 1.

However, human heart rates may influence by emotions (such as excitements, tensions, and pressures), postures (such as standing, sitting, and lying down), and activity levels. The morphology of ECG 3 (differences of the width and the height of one beat waveform) generated by the same person is various from time to time because of changes of heart rates. Thus, it is difficult to obtain consistant ECG measurements for each identification process. For example, when an ECG identification system is used in an access control device and an ECG template of the user 1 is measured and recorded in a resting state for identification usages in the future. When the user 1 tries to pass the identification authorization after doing exercise, the heart rate can be much higher than the resting state, the user then has difficulty to pass the security check under the circumstance.

There exists several ECG identification methods are suggested in the academic community, such as the time domain analysis, the frequency domain analysis, the chaos analysis and so on. The previous methods attempt to improve the ECG identification rates and to ignore the interference caused from various heart rates. However, regardless of the identification methods applied, the user 1 has to be in the same state as the state when the template made in order to provide higher identification rates. The current technologies remain unsolved to identify the same person having various heart rates. Hence, because of above reasons, the ECG identification technologies are still on the research stages and not ready to be applied in the market.

SUMMARY OF THE INVENTION

The objective of the present invention is to provide a calibration method of the ECG signals and the application program for the same, whereby unidentified ECG signals are processed before any ECG identification method so as to increase the identification rate and perform the comparison on the ECG waveforms with different heart rates generated from the same user.

In order to achieve the above objective, the method of the present invention starts with a receiving, unidentified ECG signal of a user and generates the ratio of the distance length of unidentified ECG signal and the distance length of an ECG template. Next, a trigonometric projection degree is calculated based on the ratio and it also sets a characteristic point of the unidentified ECG signal as the axis anchor point in order to attain a displacement to shift the coordinates of all ECG sample points for further trigonometric projection. Last step is to perform calibration on the unidentified ECG according to a calculated trigonometric value which corresponds with trigonometric projection degree and the attained displacement.

Compare to prior art, the advantage achieves by the present invention is providing calibration on the ECG signals of different heart rates resulting from emotions, disorders, postures or exercises. Thus, given the heart rate and posture of a user during the identification may be different from the heart rate and posture when generating the ECG template. Therefore, both width and the height of unidentified ECG signals need to be adjusted so as to match the width and the height of the ECG template for further comparison.

During the identification, various ECG waveforms result from different heart rates are calibrated with method of the present invention. In addition, multiple ECG signals of different lengths are projected to the plane of the same length according to trigonometry. Accordingly, the user is not required to maintain the same heart rate and posture producing the ECG template during identification. The tests performed by the inventor prove that given the heart rate of a user is as high as a value between over 130 bpm to 50 bpm, the calibration method of the present invention is effective to adjust the width and the height of the unidentified ECG signal so as to perform comparison of the calibrated ECG signal and the ECG template.

The present invention resolves the bottleneck of the prior art where conventionally it is difficult to compare ECG signals provided by the same person with different heart rates when applying the ECG identification. Thus the present invention is beneficial to implement ECG identification technologies in everyday life.

BRIEF DESCRIPTION OF DRAWING

The features of the invention believed to be novel are set forth with particularity in the appended claims. The invention itself, however, may be best understood by reference to the following detailed description of the invention, which describes an exemplary embodiment of the invention, taken in conjunction with the accompanying drawings, in which:

DETAILED DESCRIPTION OF THE INVENTION

Embodiments are provided in the following in order to further detail the implementations of the present invention in the summary. It should be noted that objects used in the diagrams of the embodiments are provided with proportions, dimensions, deformations, displacements and details are examples and the present invention is not limited thereto and identical components in the embodiments are the given same component numbers.

The calibration method of electrocardiogram (ECG) signal according to the present invention is implemented in an ECG identification device (as the ECG identification device 8 shown in FIG. 11A, referred as the identification device 8 in the following). The identification device 8 is used for perform calibration on the width (at horizontal axis) and/or height (at vertical axis) of a measured unidentified ECG signal (as the unidentified ECG signal 5 shown in FIG. 5) so as to increase the identification rate in the following identification process.

Figure 1:
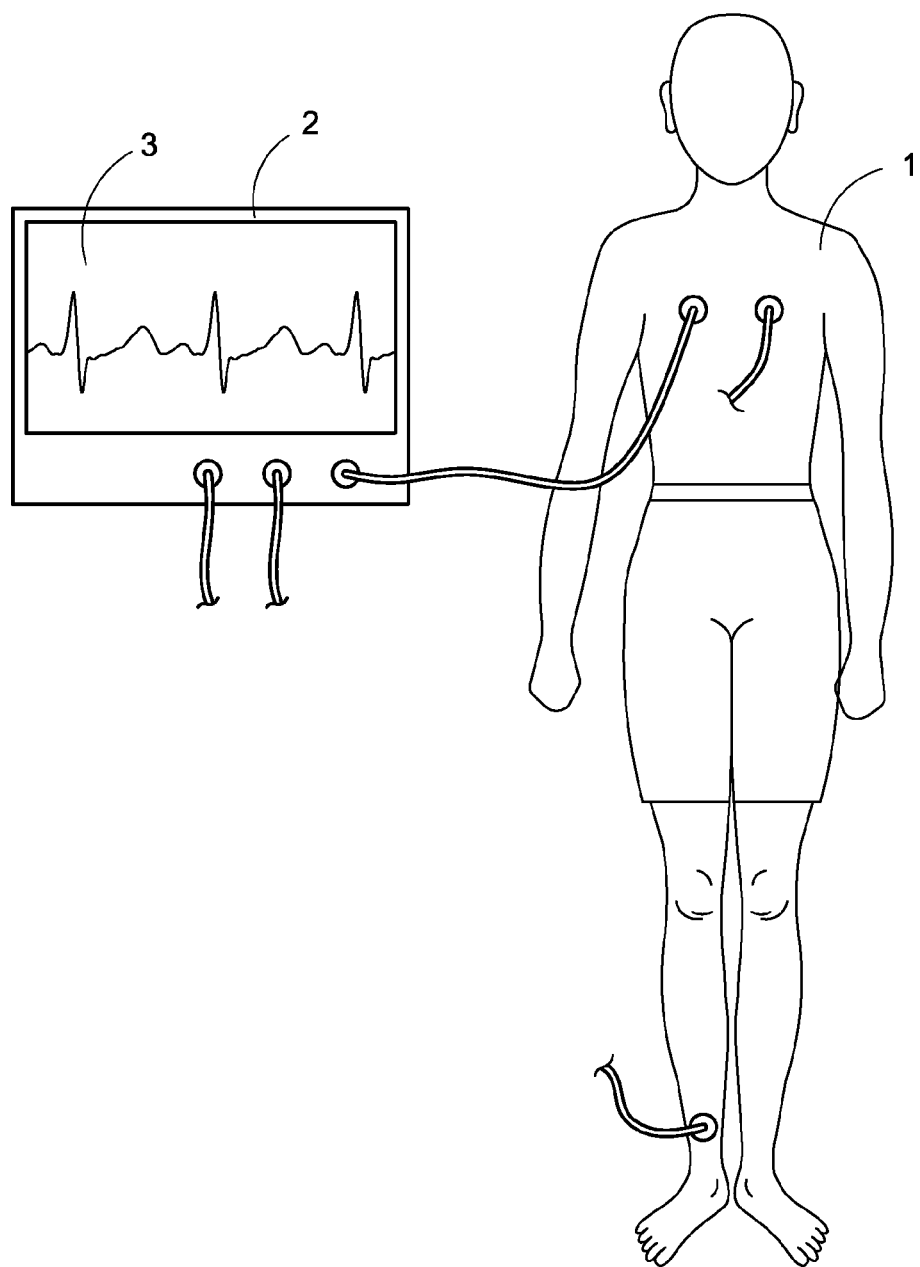
FIG. 1 is a schematic diagram of the ECG signal monitoring system according to the prior art.
Figure 2:
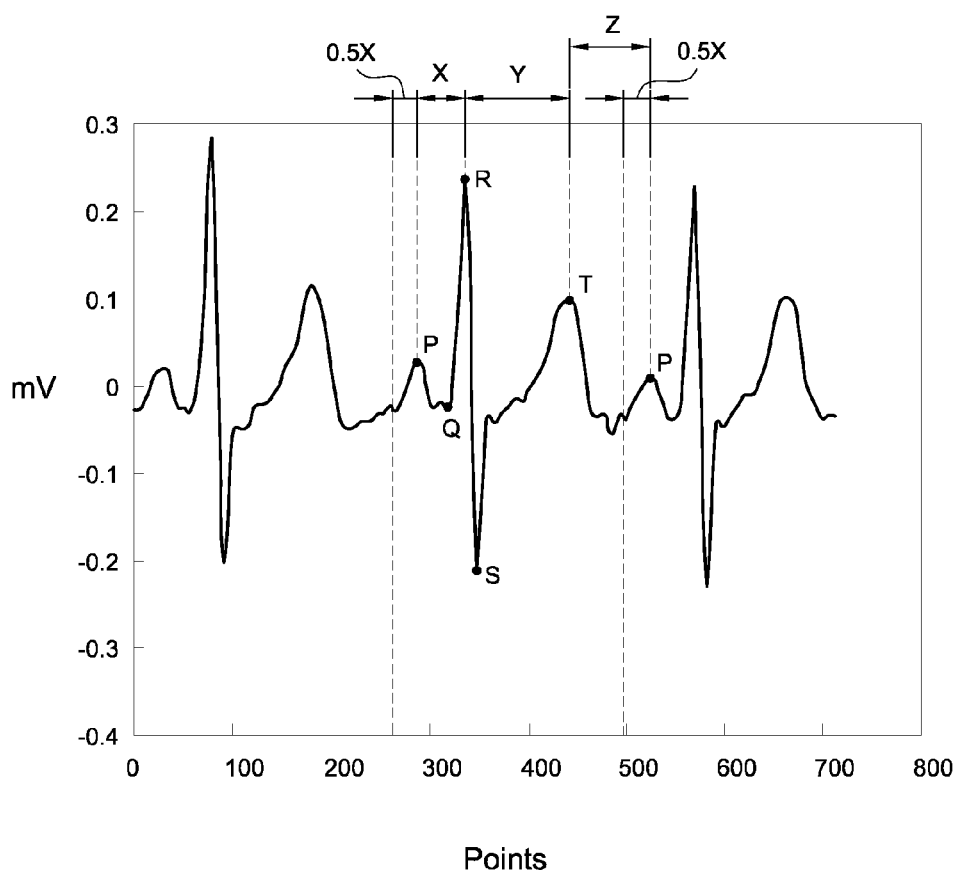
FIG. 2 is a cutting schematic diagram of the ECG signal according to the present invention.
Figure 3:
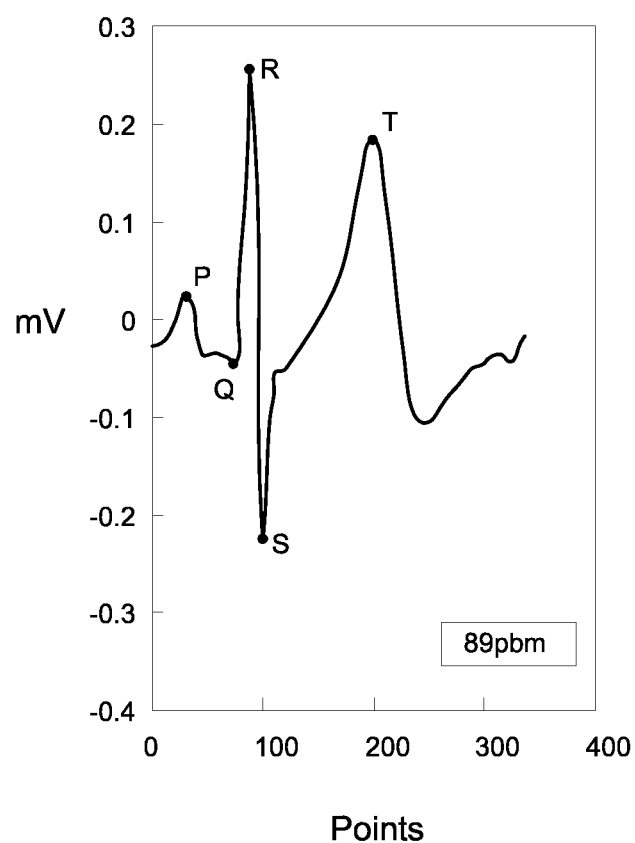
FIG. 3 is an ECG template schematic diagram according to the present invention.

FIG. 2 and FIG. 3 are respectively a cutting schematic diagram of the ECG signal and an ECG template schematic diagram according to the present invention. When the user 1 measures heart beats with the identification device 8, the identification device 8 generates a series of ECGs 3, cut and save a single ECG signal to use in future identification based on biometrics features calculated by the internal algorithm. In FIG. 3, a heart rate of 89 bpm is used as an example to generate a single ECG signal 4.

As shown in the diagram, the waveform of each heart beat has characteristic points P, Q, R, S, and T, which is well-known in physiology and is not further explained herein. When cutting, the present invention uses the R point as the marker to cut an ECG beat leftwards or rightwards. The left length is the distance (X) between the P point and the R point multiplying by 1.5×. The right length is the distance between the R point and the T point (Y) adding the distance between the T point to the P point (Z) of the next heart beats subtracting 0.5× of the distance between the P point and the R point. Thus, the distance length of the ECG signal 4 on the X-axis is defined. Further, the above mentioned cutting method is applicable to all ECG signals mentioned in the following. The distance lengths of all ECG signals on the X-axis can be generated by the above method. However, the above mentioned cutting method is a preferred embodiment tested in the experiments and is not limited thereto.

As shown in FIG. 3, the Y-axis (a.k.a. vertical axis) is the ECG signal unit (mV in general), and the X-axis (a.k.a. horizontal axis) is the distance length (point quantity) corresponding to waveform. In further details, the demonstrating heart beat is 89 bpm as an example shown in the FIG. 3. That is, the average heart beat is 1.48 beats each second, which means the time interval of each ECG signal 4 is about 0.7 second (each heart beats accounts for 0.7 second). If sample frequency rate of the identification device 8 is 500 Hz (i.e. 500 samples per second), then 500 (Hz)*0.7 (second) equals to that the ECG signal 4 which accounts for 350 points on the X-axis. In the embodiment, the distance length of the ECG signal 4 on X-axis is considered as the time interval of the ECG signal 4 or considered as the number of points on the X-axis (i.e. the time interval multiplies the sample frequency rate) and are not limited thereto.

Figure 4:
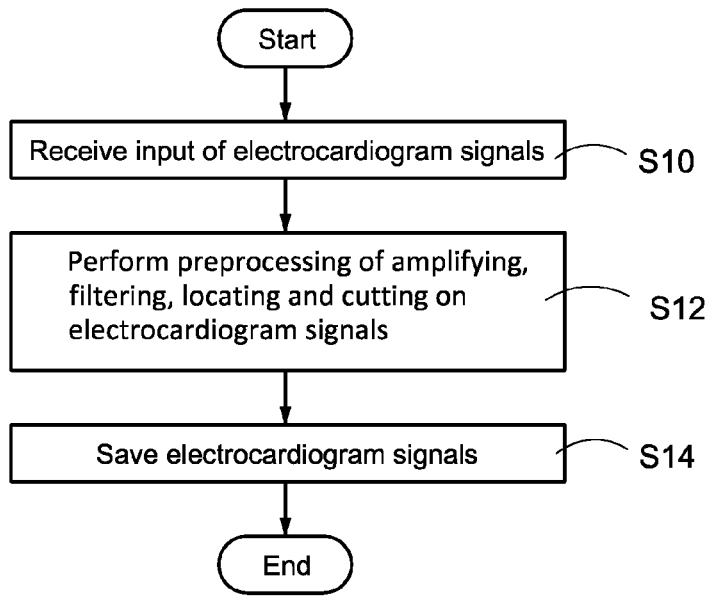
FIG. 4 is a flow chart of ECG signal processing according to the present invention.

FIG. 4 is a flow chart of ECG signal processing according to the present invention. As mentioned above, the user 1 has to measure and record an ECG template (as the ECG template 41 shown in FIG. 10) as the baseline for comparison before performing the identification. First, the identification device 8 receives the ECG input of the user 1 (step S10). Next, the identification device 8 performs pre-processing of cutting, amplifying, filtering, and locating on the ECG (step S12), and finally generates and saves at least one ECG signal 4 as shown in FIG. 3 (step S14). It should be mentioned that, if the distance length of the ECG signal 4 is not suited to be the ECG template 41, the width and/or height of the ECG signal 4 can be adjusted with the calibration method of the present invention. Then the ECG template 41 is saved into a database (not shown) for further comparison (detailed in the following).

Figure 5:
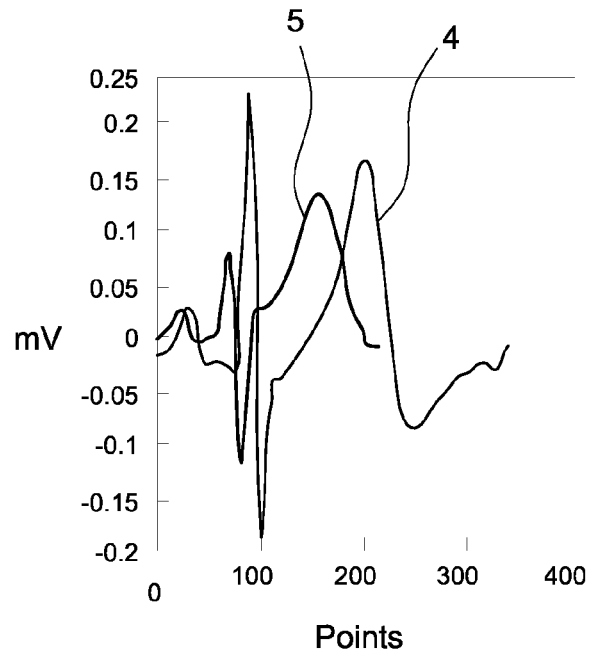
FIG. 5 is a comparison schematic diagram of ECG signals with different heart rates according to the present invention.
Figure 10:
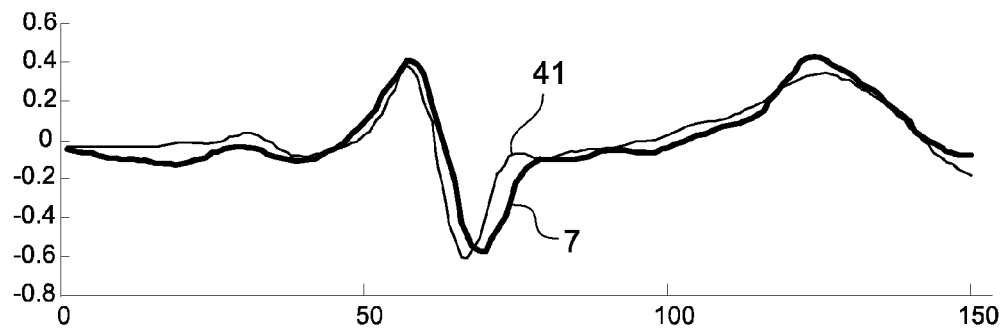
FIG. 10 is a schematic diagram of the ECG signals after the calibration according to the present invention.

FIG. 5 is a comparison schematic diagram of ECG signals with different heart rates according to the present invention. When the user 1 is measured under different emotions, physiological states, or postures, the width and/or height of the ECG signal are different along with the different heart rates. As shown in FIG. 5, if the user 1 performs ECG identification after exercises, the unidentified ECG signal 5 is shorter than the ECG signal 4 measured prior to exercise. The height of the ECG signal 4 may also changed after exercise. Under the circumstance, the identification device 8 may fail to identify human by comparing the exercise ECG signal 5 and the resting ECG signal 4 shown in FIG. 5 without any adjustment. According to the calibration method of the present invention, the ECG signal 4 is calibrated and then is saved as the ECG template 41 with a fixed distance length (for example, 150 fixed points as shown in FIG. 10). The above issue can be resolved because the unidentified ECG signal 5 is calibrated to the same distance length as the ECG template 41 prior to the identification process.

Figure 6:
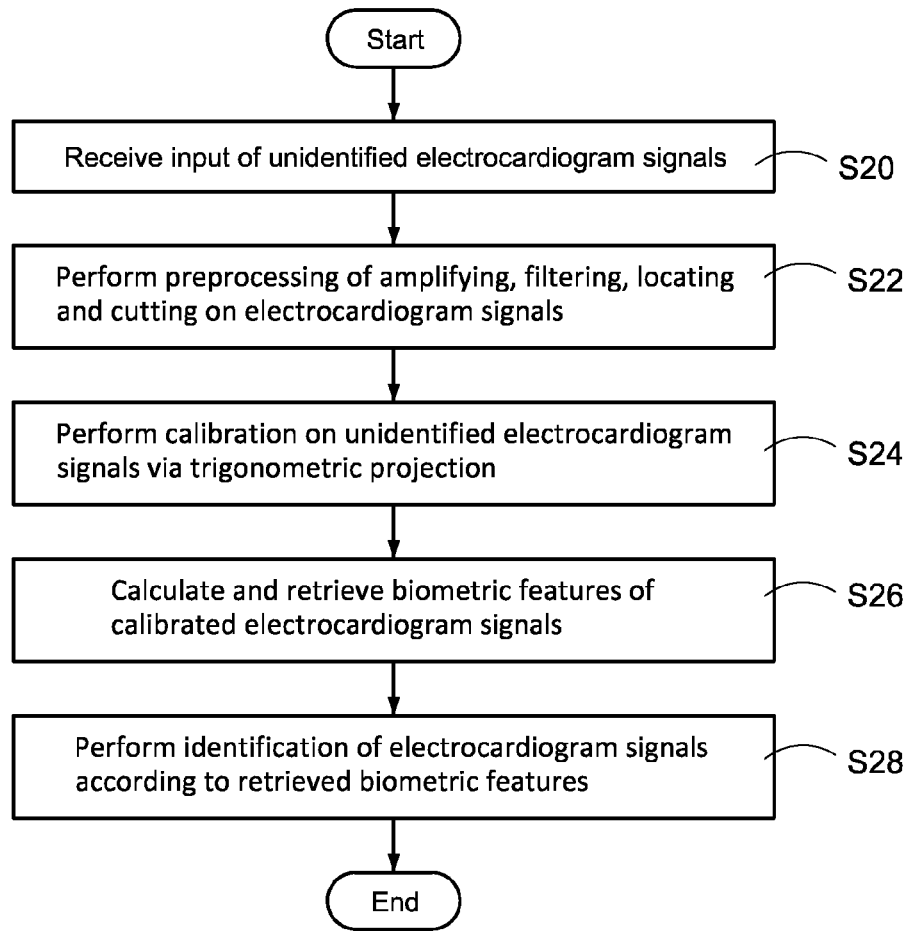
FIG. 6 is a flow chart of the ECG identification according to the present invention.

FIG. 6 is a flow chart of the ECG identification according to the present invention. First, the identification device 8 receives the input of a series of unidentified ECG signal 5 (step S20), executes pre-processing of amplifying, filtering, locating, and cutting heartbeats on the ECG (step S22), and generates the unidentified ECG signal 5 as shown in FIG. 5. Next step is the identification device 8 that performs calibration on the unidentified ECG signal 5 with a trigonometric projection (step S24). Further in details, the identification device 8 performs the calibration of the width and/or height to generate a corrected ECG signal (the calibrated ECG signal 7 shown in FIG. 10). After the step S24, biometrics features from the calibrated ECG signal 7 are retrieved and calculated (step S26). The ECG identification is performed by comparing the retrieved biometrics features from the calibrated ECG signal 7 and the ECG template 41 (step S28).

As mentioned above, according to the calibration method of the present invention, coordinates of the unidentified ECG signal 5 and/or the ECG signal 4 respectively multiply a generated trigonometric value which corresponds with a trigonometric projection degree for projecting ECG signals to a determined length on the plane where has the same distance length by changing the trigonometric projection degree. Thus, the calibration method of the present invention is applied to increase the identification rate regardless of methods used for the identification afterwards. In the present embodiment, the preferred trigonometric value is cos θ and θ is the trigonometric projection degree, but is not limited.

Figure 7A:
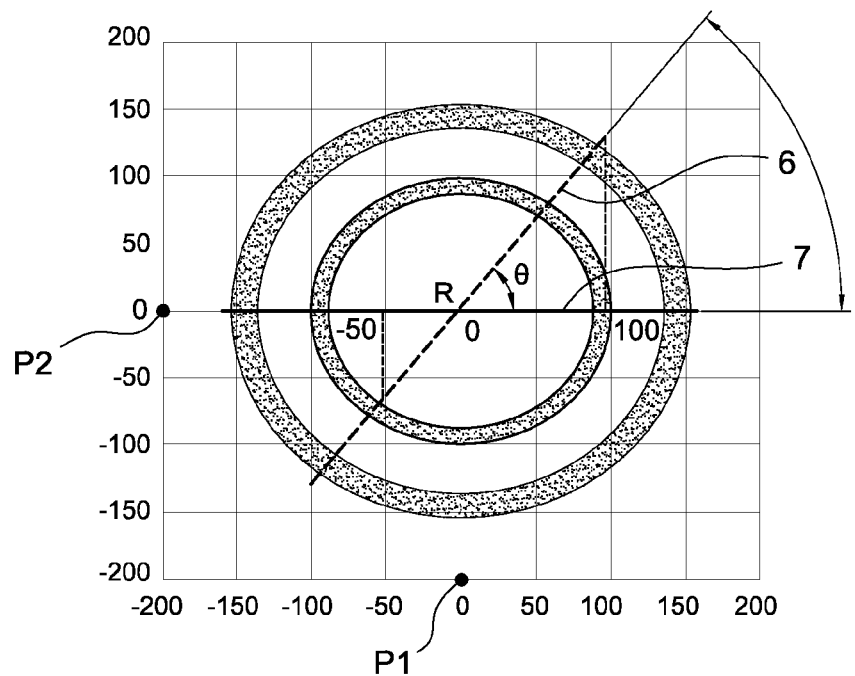
FIG. 7A is the first trigonometric schematic diagram according to the present invention.
Figure 7B:
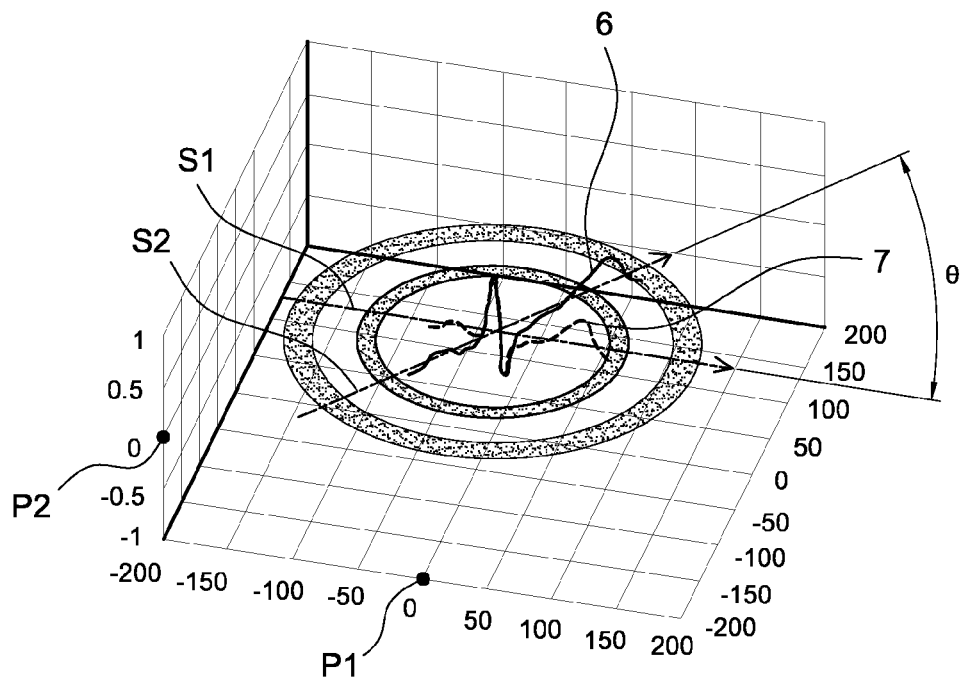
FIG. 7B is the second trigonometric schematic diagram according to the present invention.

FIG. 7A and FIG. 7B are the first trigonometric schematic diagram and the second trigonometric schematic diagram according to the present invention. FIG. 7 is used to illustrate the width calibration process. FIG. 7A shows an uncalibrated ECG signal 6 (the uncalibrated ECG signal 6 is considered as the unidentified ECG signal 5). The uncalibrated ECG signal 6 is on a second plane S2. One of a characteristic point of the uncalibrated ECG signal 6 is set to be the X-axis anchor point P1 for performing displacement of the uncalibrated ECG signal 6 on the X-axis. Next, the ratio of an uncalibrated distance length and a desired distance length is used to generate a projection angle θ. The generated projection angle θ and its cosine value are applied for projecting the distance length of the uncalibrated ECG signal 6 on a first plane S1 to attained a required width.

In the embodiment, the uncalibrated ECG signal 6 having the distance length of about 250 points is projected on the first plane S1 to generate the distance length of about 150 points, but is not limited thereto. It should be noted that the best projection result according to the experiments by the inventor is to set the R point of the uncalibrated ECG signal 6 as the X-axis anchor point P1 and to choose cos θ as the trigonometric projection function. In physically, the neighborhood area around R point in the ECG signal is the most stable region and it should be reserved more details. Hence, when the signal process approaches the anchor point R at 0° in cos θ, the coordinate changes become the smallest. So, the morphology features of the neighborhood of the R point can be better reserved by setting the R point as the X-axis anchor point P1 in calculating cos θ.

From above example, when processing the ECG signal 4, any length of the ECG signal 4 can be projected to the first plane S1 with any distance length, such as 150 points in this example, to form the ECG template 41. As shown in FIG. 7B, if the uncalibrated ECG signal 6 and the ECG signal 4 generated by the same person, the ECG template 41 matches the calibrated ECG signal 7 after the uncalibrated ECG signal 6 is adjusted. As shown in the diagram, in that case, the calibrated ECG signal 7 has the same relative height as the uncalibrated ECG signal 6, but the width is unmatched to each other. In the present invention, the calibration process includes the following steps: every signal point of the uncalibrated ECG signal 6 first subtracts the displacement, and the number of x coordinates respectively multiplies trigonometric values with a corresponding degree to generate the new projection position of each signal point on the first plane 51. The angle θ of cosine function is defined as:

$$\theta = \cos^{-1}\left(\frac{y}{x}\right);$$

wherein (y/x) is the ratio of distance length of the uncalibrated ECG signal 6 and the new distance length of the ECG template 41, and the ratio is less than 1 when y is less than or equal to x. As shown in FIGS. 7A and 7B, x is 250 points, y is 150 points, and angle θ is obtained as follows:

$$\theta = \cos^{-1}\left(\frac{150}{250}\right);$$

After calculation, the angle θ is about 53°. Thus, each X-axis coordinates of the uncalibrated ECG signal 6 subtracts the displacement, then respectively multiplies cos 53°, equals to the new position of each signal point of the calibrated ECG signal 7 whereby the calibrated ECG signal 7 is generated. The projection formula of coordinate positions can be summarized as:

New coordinate=cos θ*Old coordinate

Further, the ECG signal 4 can be transformed into the ECG template 41, the cosine angle θ is equal to $$\cos^{-1}\left(\frac{y}{x}\right),$$

wherein x is the distance length of the ECG signal 4, y is the required distance length (which is 150 points in the embodiment).

In details, the calibration method of the present invention starts with receiving the input of the uncalibrated ECG signal 6. Next, a trigonometric projection degree is generated by calculating based on the ratio of the distance length of the uncalibrated ECG signal 6 and the desired distance length on the ECG template 41. The same method can be applied on the width ratio or the height ratio. The next step is to set axis anchor point of the trigonometric projection (X-axis horizontal anchor point or Y-axis vertical anchor point) for attaining the displacement of the uncalibrated ECG signal 6 on the axis. The last step is to perform the distance length calibration on the uncalibrated ECG signal 6 according to the trigonometric value based on the degree generated by distance length ratio and the displacement. The width or height of the uncalibrated ECG signal 6 can be calibrated respectively according to the present invention. The details are summarized in flow chart (FIG. 8).

Figure 8:
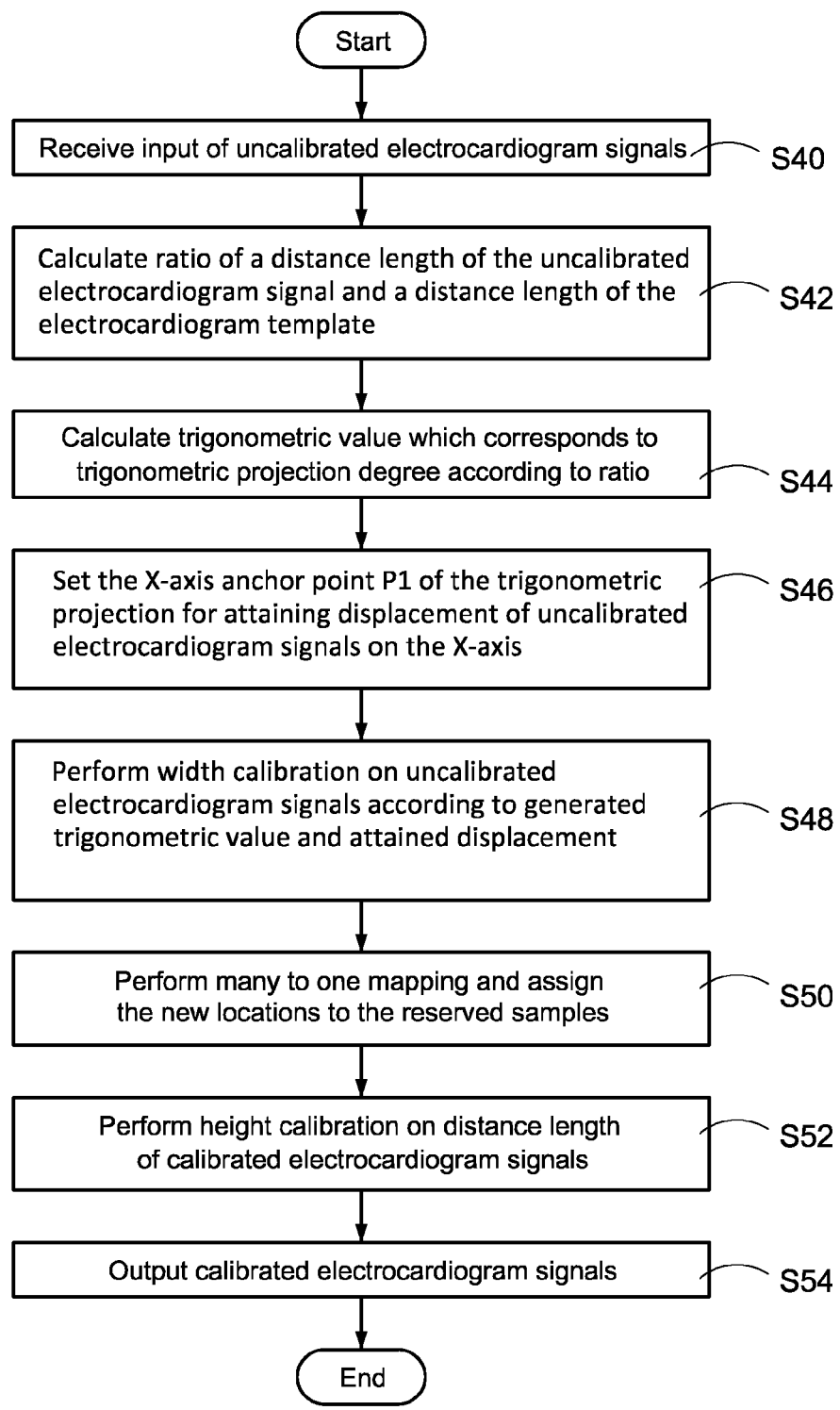
FIG. 8 is a flow chart of the width (horizontal) calibration of the ECG signal according to the present invention.

FIG. 8 is a flow chart of the width (horizontal) calibration of the ECG signal according to the present invention. First, the identification device 8 receives the input of the uncalibrated ECG signal 6 (step S40), and calculates the ratio of the distance length of the uncalibrated ECG signal 6 and the distance length of the ECG template 41 (step S42). The next step is calculating the trigonometric value which corresponds to the trigonometric projection degree according to the attained ratio from the above distance lengthes (step S44). In the embodiment, the horizontal distance length of the uncalibrated ECG signal 6 represents the time interval of the uncalibrated ECG signal 6, and the horizontal distance length of the ECG template 41 represents the time interval of the ECG template 41, but is not limited thereto.

Next step is to set the X-axis anchor point P1 of the trigonometric projection for attaining the displacement of the uncalibrated ECG signal 6 on the X-axis (step S46). In the embodiment, the R point of the uncalibrated ECG signal 6 is taken as the X-axis anchor point P1, which is not further explained herein. Nonetheless, the step S44 and the step S46 are not performed in sequence. It is also applicable to calculate the trigonometric projection degree then attain the displacement vice versa and is not limited thereto.

To explain the displacement, for example, a given the ECG signal is calculated based on the origin of the X-axis. If the coordinate position of the R point on X-axis is at the 100th point, then the R point is set as the X-axis anchor point P1. Hence, the displacement for each coordinate of the uncalibrated ECG signal 6 on the X-axis is −100. As a result, when performing the displacement, each signal point of the uncalibrated ECG signal 6 subtracts 100 to align the R point as a new origin. Then the calibrated ECG signal 7 is aligned with the ECG template 41 at the R point. Hence, each coordinate of the ECG template 41 subtracts a displacement (100), or each coordinate of the calibrated ECG signal 7 adds a displacement (100), and is not limited thereto.

After the step S44 and the step S46, the identification device 8 performs the width calibration on the uncalibrated ECG signal 6 according to the mentioned calculated trigonometric projection degree and the displacement on the X-axis (step S48).

After the step S48, the identification device 8 performs a many to one mapping function, and assigns the new locations to the reserved samples (step S50). In further details, the step S50 is to deal with many to one mapping problem. It selects one out of values projecting on the same new location. For example, if θ is 53°, then cos 53° is about 0.6, the 208th point multiplies cos 53° is 124.8; and the 207th point multiplies cos 53° is 124.2. In view of the identification device 8, points 208, 207 are both projected to point 124 on the new location. Thus, in the step S50, the identification device 8 selects the point closest to the anchor point (which is 124.2 in the example) as the point 124, and point 124.8 is then discarded.

Similarly, the last step is to perform height calibration on the vertical distance length of the horizontal calibrated ECG signal 7 (step S52), then to output the calibrated ECG signal 7 (step S54) for performing further identification.

Figure 9:
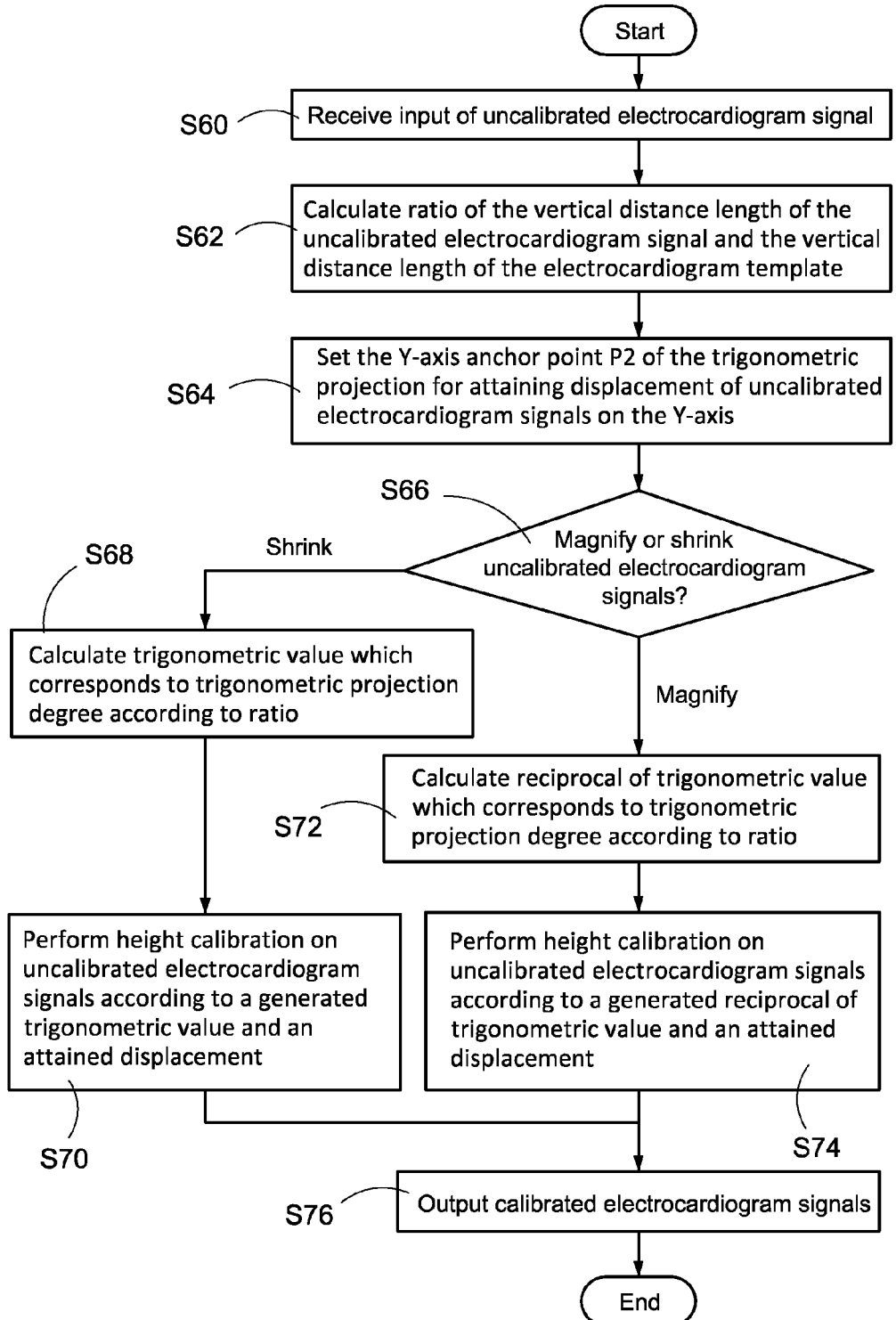
FIG. 9 is a flow chart of the height (vertical) calibration of the ECG signal according to the present invention.

FIG. 9 is a flow chart of the height (vertical) calibration of the ECG signal according to the present invention. The height calibration of the uncalibrated ECG signal 6 starts with the identification device 8 first receiving the input of the uncalibrated ECG signal 6 (step S60). The next step is to calculate the ratio of the vertical distance length of the uncalibrated ECG signal 6 and the vertical distance length of the ECG template 41 (step S62). In further details, during the height calibration, the vertical distance length of the uncalibrated ECG signal 6 is normalized by referring the vertical distance length of ECG template 41. Preferably, the distance length of the uncalibrated ECG signal 6 is the vertical distance between S point and R point of the uncalibrated ECG signal 6, and the distance length of the ECG template 41 is the vertical distance between S point and R point of the ECG template 41. The above mentioned descriptions are preferred embodiments of the present invention and are not limited thereto.

After the step S62, the Y-axis anchor point (the Y-axis anchor point P2 shown in FIG. 7) is set for attaining the displacement of the uncalibrated ECG signal 6 on the Y-axis (step S64). The experiments performed by the inventor show that a flat region is observed between the S point and the T point of the ECG signal (not shown in the diagram). Selecting a point on the flat region as the Y-axis anchor point P2 is one of the best practices, but is not limited thereto.

Next, the method determines if the vertical distance length of uncalibrated ECG signal 6 should be magnified or shrunk (step S66). If the distance length of uncalibrated ECG signal 6 should be shrunk, the trigonometric value which corresponds to the trigonometric projection degree is calculated according to the above ratio (step S68). The height calibration is performed on the uncalibrated ECG signal 6 according to the calculated trigonometric value which corresponds with trigonometric projection degree and the displacement (step S70).

If the uncalibrated ECG signal 6 is to be magnified, the reciprocal of the trigonometric value which corresponds with the trigonometric projection degree according to the attained ratio from the above distance lengths is calculated (step S72). The height calibration is performed on the uncalibrated ECG signal 6 according to the reciprocal of the trigonometric value which corresponds with trigonometric projection degree and the displacement (step S74).

In details, the trigonometric value in the embodiment is cos θ, and the reciprocal of the trigonometric value is the reciprocal of cos θ, $$\text{i.e. } \left(\frac{1}{\cos\theta}\right).$$

The cosine angle θ (the trigonometric projection degree) is:

$$\theta = \cos^{-1}\left(\frac{b}{a}\right),$$

wherein (b/a) is the ratio of the smaller distance length of the uncalibrated ECG signal 6 and the larger distance length of the ECG template 41, and the ratio is less than 1. After the step S70 or the step S74, the calibrated ECG signal 7 is generated. Those steps (S70 or S74) calibrates the vertical distance length of the calibrated ECG signal 7, also the calibrated ECG signal 7 is the output at the end (step S76).

FIG. 10 is a schematic diagram of the ECG signals after the calibration according to the present invention. Proven with experiments performed by the inventor, the calibration method of the present invention resolves the identification rate issue resulting from the differences of ECG signals generated by the same person under different heart rates or postures. In FIG. 10, the ECG template 41 and the calibrated ECG signal 7 are respectively generated. The diagram shows that the width and/or the height of the calibrated ECG signal 7 are very similar to those of the ECG template 41. The corresponding characteristic points are selected respectively from two ECG signals 41, 7 for performing the comparison analysis, which leads to improved identification rates.

Figure 11A:
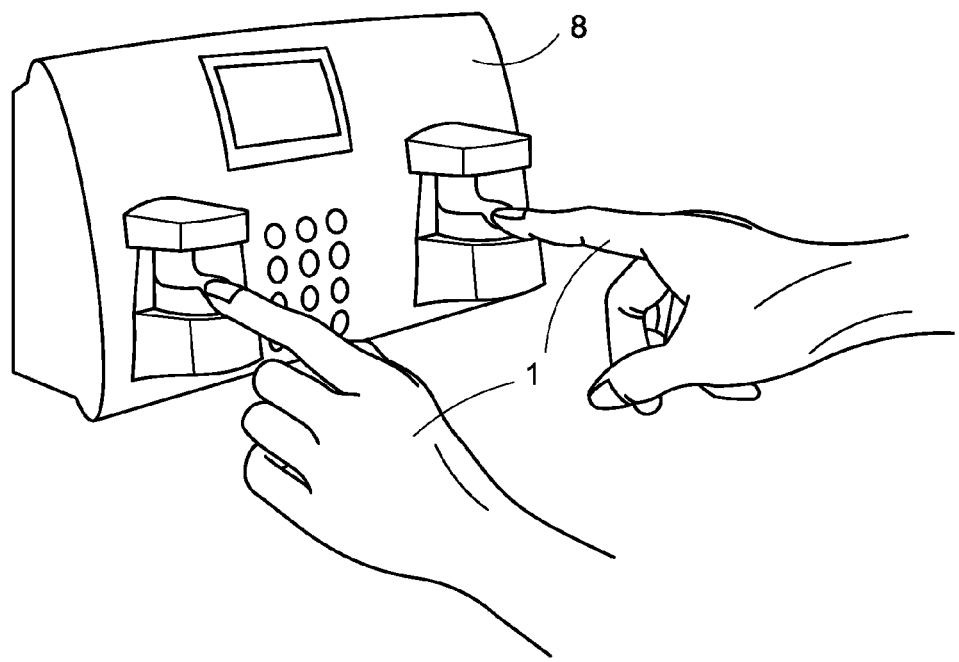
FIG. 11A is a utilization schematic diagram of the first preferred embodiment according to the present invention.
Figure 11B:
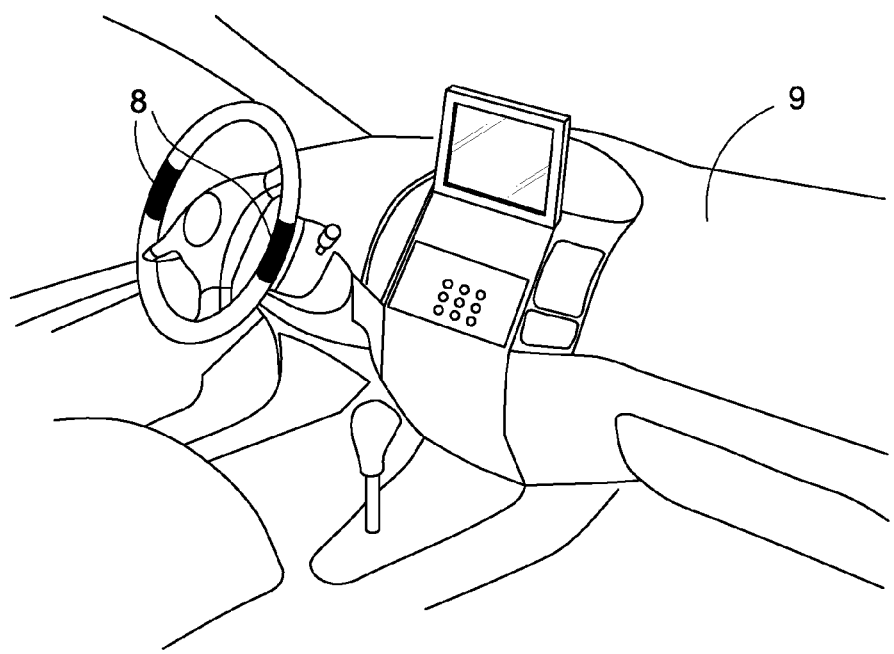
FIG. 11B is a utilization schematic diagram of the second preferred embodiment according to the present invention.
Figure 11C:
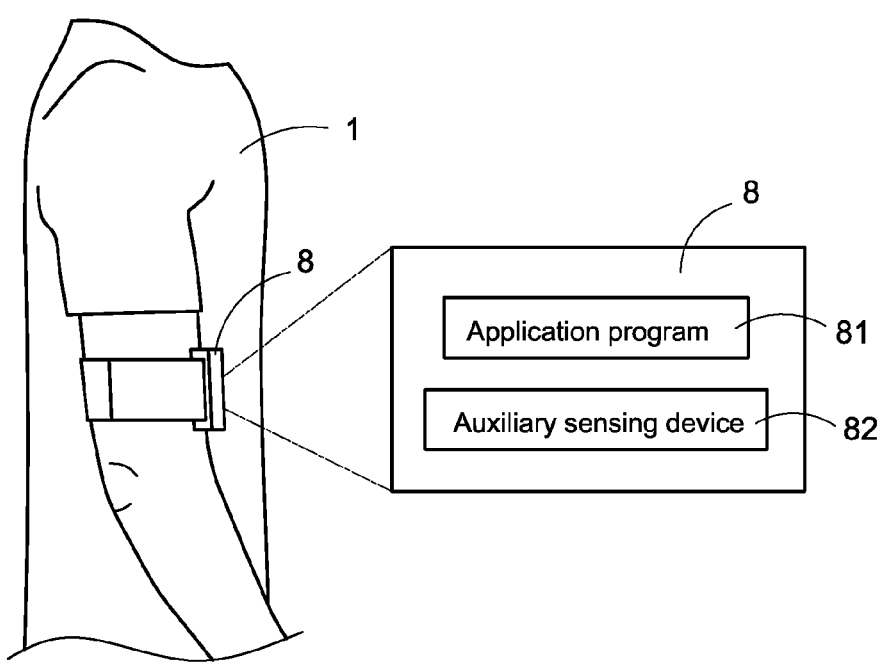
FIG. 11C is a utilization schematic diagram of the third preferred embodiment according to the present invention.

FIG. 11A, FIG. 11B and FIG. 11C are utilization schematic diagrams of the first preferred embodiment, the second preferred embodiment and the third preferred embodiment according to the present invention. The present invention further provides an application program 81 (the application program 81 shown in FIG. 11C). The application program 81 operates in the identification devices. When the application program 81 is loaded and executed in the identification device 8, the calibration method of the ECG signals of the present invention is implemented and the detailed steps of the calibration method are not further explained herein.

The identification device 8 in FIG. 11A can be set at the gate of a building as an access control system. Regardless of the physical states of the user 1 upon providing the ECG template 41 and the physical states of the user 1 upon accessing authorization, the application program 81 performs calibration on the unidentified ECG signal 5 before performing the identification so as to increase the identification rate of the access control system and provide a new access control system in daily life.

As shown in FIG. 11B, the identification device 8 can be built to personal devices of the user 1 such as a car 9 so as to enhance the security mechanism of the car 9. As shown in the diagram, the user 1 provides the ECG template 41 in a standing posture and the unidentified ECG signal 5 is measured in a sitting or lying down posture. Although above factors results from different ECG signals in the width and the height, the resulting ECG signals are normalized by the application program 81 via executing the calibration method of the present invention to improve the identification rate. As a result, regardless of which posture the user 1 has in the car 9 upon measuring the ECG signals, the identification device 8 is able to perform identification successfully for starting up the car 9.

Further, the identification device 8 having the application program 81 can be installed in a general bicycle or a bicycle in a gym (not shown in the diagram), or the application program 81 can be written to the chipset installed in a bicycle for the convenience upon measuring and experimenting. Thus, the user 1 is identified or verified oneself at different the heart rates during exercise, and the ECG signals can be calibrated to facilitate commercial, research and experiment proposes.

As shown in FIG. 11C, the identification device 8 is installed with the application program 81, also installed with an auxiliary sensing device 82. In the embodiment, the auxiliary sensing device 82 is, for example, an accelerometer or a gyro, but is not limited thereto.

ECG signals of the user 1 are affected by the different emotions, physical status, postures upon measurements. Potentially, the user 1 may also sit or lay down upon measuring to provide a position-related ECG morphology, so the doctor is unable to perform the correct diagnosis on remote healthcare applications when the current posture of user 1 is unknown. Thus, as shown in FIG. 11C, the identification device 8 determines the adjustment of the height of the uncalibrated ECG signal 6 resulting by the postures of the user 1 via the auxiliary sensing device 82, i.e., an accelerometer or a gyro. Thus, in addition to perform the biometric comparison, the identification device 8 is also useful in helping the doctors to avoid misinterpretation of ECG signals caused by different postures upon measurements in remote monitoring devices. For another example, false alarm may happen if the ECG signals measured from a user A in standing similar to the ECG signals measured from a user B in the laying position. At this point, the auxiliary sensing device 82 is useful in confirming the current posture of the user during access, which further improves the accuracy of the ECG identification.

A skilled person has various changes and modifications according to the described embodiments. It is intended to include all such variations, modifications and equivalents which fall within the scope of the invention, as defined in the accompanying claims.

What is claimed is:

1. A calibration method of electrocardiogram signals, utilized in an electrocardiogram identification or verification device, an electrocardiogram template of a user saved in the electrocardiogram identification or verification device, the calibration method of the electrocardiogram signals comprising:
   a) receiving an input of an uncalibrated electrocardiogram signal;
   b) generating a trigonometric projection degree by calculating a ratio of a distance length of the uncalibrated electrocardiogram signal and a distance length of the electrocardiogram template;
   c) setting an axis anchor point of trigonometric projection for attaining a displacement of the uncalibrated electrocardiogram signal on the axis; and
   d) performing calibration of the distance length on the uncalibrated electrocardiogram signal according to a generated trigonometric value which corresponds with the trigonometric projection degree and the attained displacement,
   wherein the distance length of the uncalibrated electrocardiogram signal is the time interval of the uncalibrated electrocardiogram signal, the distance length of the electrocardiogram template is the time interval of the electrocardiogram template in the step b, the axis is X-axis in the step c, and the width calibration is performed on the uncalibrated electrocardiogram signal in the step d.

2. The calibration method of the electrocardiogram signals of claim 1, wherein the method further comprising a step e after the step d: performing calibration on the distance length of an electrocardiogram signal to assure the distance length of the calibrated electrocardiogram signal equals to the distance length of the electrocardiogram template.

3. The calibration method of the electrocardiogram signals of claim 1, wherein the R point of the uncalibrated electrocardiogram signal is X-axis anchor point of the trigonometric projection in the step c.

4. The calibration method of the electrocardiogram signals of claim 3, wherein the trigonometric value is cos θ, the trigonometric projection degree θ is $$\cos^{-1}\left(\frac{y}{x}\right),$$

wherein $$\left(\frac{y}{x}\right)$$

is the ratio of the distance length of the uncalibrated electrocardiogram signal and the distance length of the electrocardiogram template, the distance length y is less than or equal to the distance length x, and the ratio is less than 1.

5. The calibration method of the electrocardiogram signals of claim 4, wherein each signal point of the uncalibrated electrocardiogram signal subtracts the displacement on the X-axis, then each x coordinate multiplies the trigonometric value which corresponds with the trigonometric projection degree in the step d.

6. A calibration method of electrocardiogram signals, utilized in an electrocardiogram identification or verification device, an electrocardiogram template of a user saved in the electrocardiogram identification or verification device, the calibration method of the electrocardiogram signals comprising:
   a) receiving an input of an uncalibrated electrocardiogram signal;
   b) generating a trigonometric projection degree by calculating a ratio of a distance length of the uncalibrated electrocardiogram signal and a distance length of the electrocardiogram template;

c) setting an axis anchor point of trigonometric projection for attaining a displacement of the uncalibrated electrocardiogram signal on the axis; and d) performing calibration of the distance length on the uncalibrated electrocardiogram signal according to a generated trigonometric value which corresponds with the trigonometric projection degree and the attained displacement, wherein the distance length of the uncalibrated electrocardiogram signal is the vertical distance between S point and R point of the uncalibrated electrocardiogram signal as height and the distance length of the electrocardiogram template is the vertical distance between S point and R point of the electrocardiogram template as height in the step b, the axis is Y-axis in the step c, and the height calibration is performed on the uncalibrated electrocardiogram signal in the step d.

7. The calibration method of the electrocardiogram signals of claim 6, wherein the Y-axis anchor point of the trigonometric projection is located at a flat region between S point and T point of the uncalibrated electrocardiogram signal in the step c.

8. The calibration method of the electrocardiogram signals of claim 7, wherein further comprising following steps:

e) determining if the uncalibrated electrocardiogram signal is to be magnified or shrinked;

f) calculating a reciprocal of a trigonometric value which corresponds with the trigonometric projection degree according to a ratio of the distance length of the uncalibrated electrocardiogram signal and the distance length of the electrocardiogram template if the uncalibrated electrocardiogram signal is to be magnified; and g) performing the height calibration on the uncalibrated electrocardiogram signal according to the generated reciprocal of the trigonometric value which corresponds with the trigonometric projection degree and the attained displacement following step f.

9. The calibration method of the electrocardiogram signals of claim 8, wherein the trigonometric value which corresponds with the trigonometric projection degree is cos θ, and the reciprocal of the trigonometric value which corresponds with the trigonometric projection degree is $$\left(\frac{1}{\cos\theta}\right),$$

the trigonometric projection degree θ is $$\cos^{-1}\left(\frac{b}{a}\right),$$

wherein $$\left(\frac{b}{a}\right)$$

is the ratio of the distance length of the uncalibrated electrocardiogram signal and the distance length of the electrocardiogram template, the distance length b is less than or equal to the distance length a, and the ratio is less than 1.

10. The calibration method of the electrocardiogram signals of claim 9, wherein, all Y-axis coordinates of the uncalibrated electrocardiogram signal subtract the displacement of the Y-axis, then respectively each y coordinate multiplies the trigonometric value which corresponds with the trigonometric projection degree in the step d; and all Y-axis coordinates of the uncalibrated electrocardiogram signal subtract the displacement of the Y-axis, then respectively each y coordinate multiplies the reciprocal of the trigonometric value which corresponds with the trigonometric projection degree in the step g.

11. The calibration method of the electrocardiogram signals of claim 6, wherein the electrocardiogram identification or verification device comprises an accelerometer or a gyro, the step d and the step g further determining the levels of adjustment on height of the uncalibrated electrocardiogram signal according to user postures via the accelerometer or the gyro.

12. An application program saved in an electrocardiogram identification or verification device, when the electrocardiogram identification or verification device loaded and executed in the application program a calibration method of electrocardiogram signals is performed, wherein an electrocardiogram template of a user is saved in the electrocardiogram identification or verification device, and the calibration method of the electrocardiogram signals comprising:

a) receiving an input of a uncalibrated electrocardiogram signal;

b) generating a trigonometric projection degree by calculating a ratio of a distance length of the uncalibrated electrocardiogram signal and a distance length of the electrocardiogram template;

c) setting an axis anchor point of trigonometric projection for attaining a displacement of the uncalibrated electrocardiogram signal on the axis; and d) performing calibration of the distance length on the uncalibrated electrocardiogram signal according to a generated trigonometric value which corresponds with the trigonometric projection degree, and the attained displacement, wherein the distance length of the uncalibrated electrocardiogram signal is the time interval of the uncalibrated electrocardiogram signal, the distance length of the electrocardiogram template is the time interval of the electrocardiogram template in the step b, the axis is X-axis in the step c, and the width calibration is performed on the uncalibrated electrocardiogram signal in the step d.

* * * * *